United States Patent [19]
Thornton

[11] Patent Number: 5,536,247
[45] Date of Patent: Jul. 16, 1996

[54] METHOD OF TREATING CARDIAC CONDUCTION DEFECTS

[75] Inventor: Arnold Thornton, Roseville, Minn.

[73] Assignee: Scimed Life Systems, Inc., Maple Grove, Minn.

[21] Appl. No.: 431,385

[22] Filed: Apr. 28, 1995

Related U.S. Application Data

[63] Continuation of Ser. No. 74,889, Jun. 10, 1993, abandoned.

[51] Int. Cl.⁶ .................................................. A61M 31/00
[52] U.S. Cl. ............................................. 604/49; 604/53
[58] Field of Search ............................. 604/41, 49, 53, 604/96–109; 128/702, 705

[56] References Cited

U.S. PATENT DOCUMENTS

| | | | |
|---|---|---|---|
| 4,299,226 | 11/1981 | Banka | 604/53 |
| 4,456,000 | 6/1984 | Schjeldahl et al. | 604/53 |
| 4,860,743 | 8/1989 | Abela | 606/16 |
| 4,883,058 | 11/1989 | Ruiz | 604/53 |
| 5,025,786 | 6/1991 | Siegel | 128/673 |
| 5,041,109 | 8/1991 | Abela | 606/15 |
| 5,140,987 | 8/1992 | Schuger et al. | 606/15 |
| 5,275,597 | 1/1994 | Higgins et al. | 607/116 |

OTHER PUBLICATIONS

Cardiology Clinics, vol. 2, No. 1, Feb. 1984, "Disorders of Atrioventricular Conduction in Acute Myocardial Infarction, Effect on Prognosis and Management", pp. 29–34.

Medical Clinics of North America, vol. 68, No. 4, Jul. 1984, "Cardiac Arrhythmias", Jul. 1984, pp. 1000–1009.

*Primary Examiner*—John D. Yasko
*Attorney, Agent, or Firm*—Robert Atkinson

[57] ABSTRACT

A method of treating cardiac conduction defects and/or congestive heart disease. The method involves identifying the branch arteries that feed blood to the specialized cardiac conduction cells of the heart and/or to any ischemic regions of the heart. Any occlusions in these arteries are then opened using conventional PTCA devices and procedures which, prior to the present invention, have not been used to treat occlusions in the branch arteries that supply blood to the heart.

55 Claims, 12 Drawing Sheets

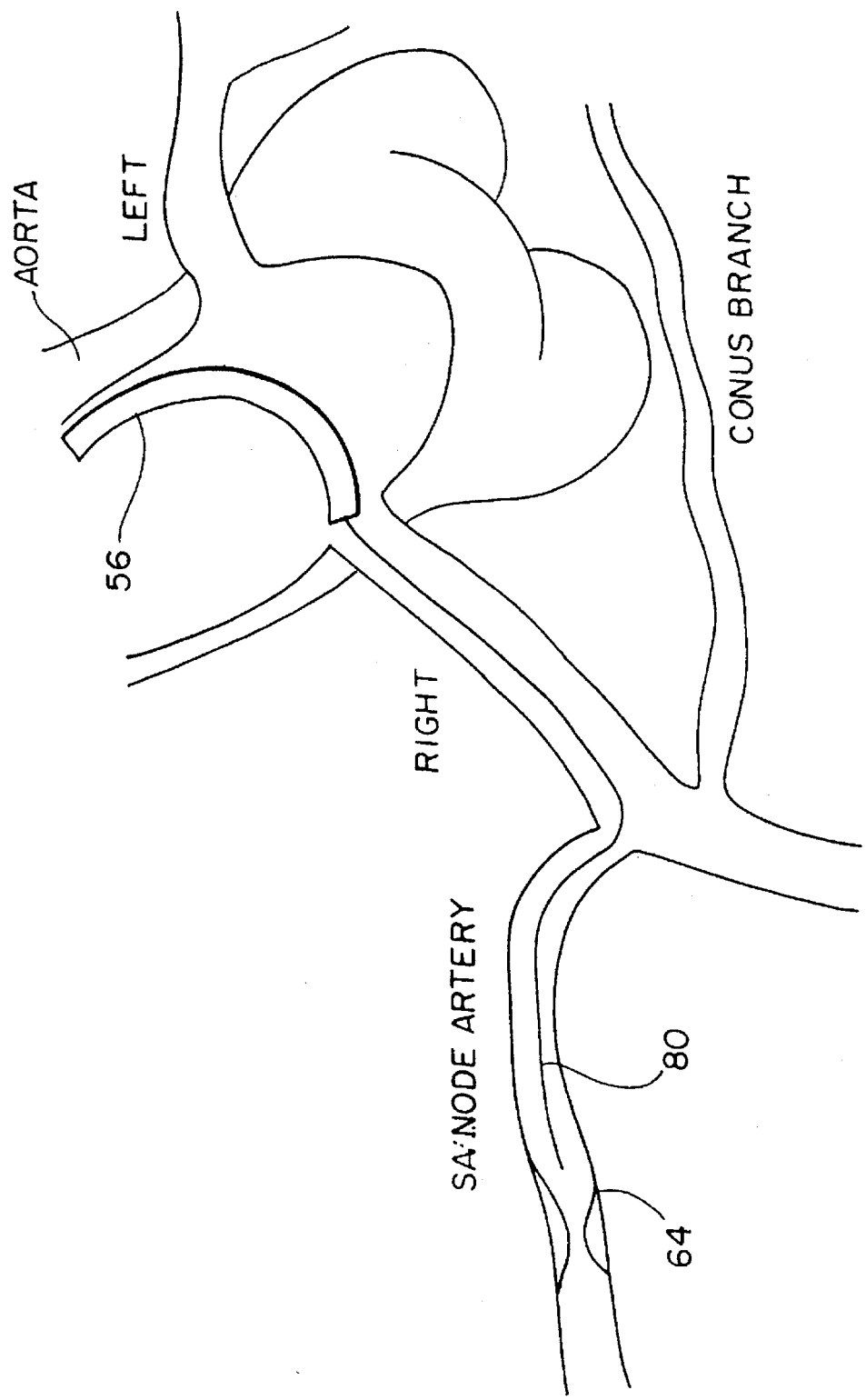

METHOD OF TREATING CARDIAC CONDUCTION DEFECTS

This is a continuation of application Ser. No. 08/074,889, filed Jun. 10, 1993 now abandoned.

BACKGROUND OF THE INVENTION

1. Field of the Invention

This invention relates in general to cardiac conduction defects in the heart. More particularly, it relates to a method of treating cardiac conduction defects by treating occlusions (both partial and total) in the arteries supplying blood to the specialized cardiac conduction cells of the heart. The specialized cardiac cells play an active role in controlling the cardiac cycle by receiving electrical impulses and conducting them throughout the heart. The cardiac cells are generally found in the conduction nodes, the conducting fibers that connect the conduction nodes, and portions of the myocardium muscle layer of the heart.

The term "occlusion" as used throughout this disclosure is intended to refer to both partial and total occlusions.

2. General Description of the Art

The cardiovascular system, also known as the blood-vascular system, generally includes the heart, a tortuous network of blood vessels and the blood flowing therein. The heart is a hollow muscle that functions as the central organ of the entire cardiovascular system. FIG. 1 illustrates the three layers that make up the walls of a normal human heart. One layer is the epicardium which is the layer of serous pericardium on the surface of the heart. The second layer is the myocardium which is a thick contractile middle layer having specially constructed and arranged cardiac cells and muscle cells. The third layer is the endocardium which includes the endothelial lining membrane connected to a connective tissue bed.

The heart pumps blood through the vascular system by periodically contracting and relaxing. FIG. 2 is a diagram illustrating how blood circulates throughout the human body through a network of tubes known generally as arteries, capillaries and veins. The arteries end in very minute vessels known as arterioles which open into the microscopic capillaries. After the blood has passed through the capillaries, it is collected into a series of larger vessels know as veins, and the veins return the blood to the heart. The terms "blood circulation" are generally used to describe how the blood moves through the heart and the above-described blood vessels.

FIG. 2 also illustrates a diagrammatic representation of the human heart 20. As shown in FIG. 2, the heart 20 is divided by a septum wall 22 into right and left halves, and each half is further divided into upper and lower cavities. The upper cavities are referred to as auricles or atria, and the lower cavities are referred to as ventricles. Thus, the heart 20 is divided into four cavities known generally as the right atrium 24, the left atrium 26, the right ventricle 28, and the left ventricle 30. In general, the right half of the heart contains venous or impure blood 32, and the left half of the heart contains arterial or pure blood 34.

The diagrammatic representation of the heart 20 shown in FIG. 2 is illustrated in further detail in FIG. 3. FIG. 3 shows that the four cavities of the heart are further separated by one-way valves which shutoff blood flow when they are closed and allow blood to flow in one direction when they are open. The right atrium 24 is separated from the right ventricle 28 by the tricuspid valve 36, and the left atrium 26 is separated from the left ventricle 30 by the mitral valve 38. The right ventricle 28 is separated from the pulmonary aorta by the pulmonary semilunar valve 40, and the left ventricle 30 is separated from the systemic aorta by the aortic semilunar valve 42.

Referring again to FIGS. 2 and 3, the heart 20 pumps pure blood 34 from the left ventricle 30 into the systemic arteries which carry the blood to the systemic capillaries, the intestinal capillaries and the hepatic capillaries. As the pure blood 34 passes through the capillaries, it provides the surrounding body tissues with the materials they need for growth and nourishment. The primary material supplied is oxygen. At the same time, the pure blood 34 receives from the body tissues the waste products resulting from their metabolism. Accordingly, the pure arterial blood 34 changes to impure venous blood 32 as it flows through the capillaries. The impure blood 32 is collected by the veins of the body and returned to the right atrium 24. As best shown in FIG. 3, impure blood is supplied to the right atrium via the superior vena cava and the inferior vena cava. The superior vena cava returns blood from the upper half of the body, and the inferior vena cava returns blood from the lower half of the body.

The impure blood then passes through the right atrium 24 to the right ventricle 28 which pumps it to the lungs (not shown) via the pulmonary arteries and the pulmonary capillaries. In the lungs, the impure blood is cleansed and oxygenated and returned via the pulmonary veins to the left atrium 24 of the heart. The left atrium 24 passes the pure blood 32 to the left ventricle 30 which pumps it out to the systemic arteries to begin the circulation process again.

The cardiac cycle may be defined as a complete heartbeat consisting of contraction (systole) and relaxation (diastole) of the atria and the ventricles. FIG. 4 illustrates the pressure-volume loops for the right and left ventricles as the heart goes through a complete cardiac cycle. The area enclosed in the loop is a measure of the work done by the heart in ejecting blood. Diagrammatic representations of the heart during one cardiac cycle surround the loops and are linked by arrows with their appropriate position (in time) on the loop. The contracting portions of the heart are shaded.

In all vertebrates, the cardiac cycle can be divided into four phases. The first phase of the cardiac cycle is known as the filling phase or atrial systole. In the atrial systole phase, the tricuspid valve and the mitral valve are shut, and the atria are filling with blood. Ventricular pressure at the start of this phase is low and falling. When ventricular pressure falls below atrial pressure, the tricuspid and mitral valves open, and blood flows rapidly into the right and left ventricles. The end of the ventricular relaxation phase (diastole) is marked by the start of ventricular contraction (systole) which increases ventricular pressure and shuts the atrioventricular valves.

The second phase is known as isovolumetric contraction. In the isovolumetric phase, the pressure in the ventricles increases, but no ejection of fluid takes place. As shown in FIG. 4, the tricuspid valve 36, mitral valve 38, pulmonic valve 40 and aortic valve 42 are closed. The ventricular muscle contracts, developing tension, and the pressure of the contained blood in the ventricle increases. This phase generally represents the period between the start of ventricular contraction (systole) and the opening of the pulmonic and aortic valves.

The third phase of the cardiac cycle is known as ventricular ejection. During this phase, the pressure in the ventricles exceeds the pressure in the atria, thus forcing the pulmonic and aortic valves 40, 42 open and pumping blood into the pulmonary and systemic arteries. The amount of blood pumped by a single ventricle during ejection is known as the stroke volume, which is usually measured in milliliters. The cardiac output, typically measured in liters per minute, is a product of the stroke volume multiplied by the heart rate. Normal cardiac output is approximately 4 to 8 liters per minute.

The fourth and final phase of the cardiac cycle is known as isovolumetric ventricular relaxation. During this phase, all inflow and outflow heart valves are closed, and ventricular pressure falls rapidly as the ventricular muscles relax. Some subatmospheric pressure can occur in this phase due to "elastic recoil" of the ventricle walls.

The heartbeat results from the development and organized control of ionic current flow through the specialized cardiac cells of the heart. This organized current flow allows the heart to pump blood by initiating the cyclical contraction and relaxation of the myocardial muscles surrounding the atria and ventricles of the heart. This organized current flow corresponds to the muscle contractions and relaxations of the cardiac cycle.

The specialized cardiac cells are generally found in the conduction nodes, the conducting fibers that connect the conduction nodes, and portions of the myocardial muscle layer of the heart. The cardiac conduction cells generally go through two electrical processes known as depolarization and repolarization. During depolarization, the cells are stimulated and the myocardium contracts. During repolarization, the myocardium relaxes.

FIG. 5 illustrates the specialized conduction system of the heart. The heart's conduction system stimulates and coordinates muscle contractions by conducting electrical impulses through the heart. The electrical impulses originate in the autonomic nervous system, and travel first to the sinoatrial (SA) node located in the right atrium 24. The sinoatrial node is referred to as the heart's "pacemaker" because it triggers and coordinates the electrical impulses that are sent throughout the heart.

Impulses from the sinoatrial node are initially sent to the right and left atria 24, 26 through the internodal tracts. The sinoatrial node normally fires between 60 and 100 times per minute. After the right and left atria 24, 26 have been stimulated, the impulse travels to the atrioventricular node which is located in the right atrium 24 near the tricuspid valve 36. The atrioventricular node delays the impulse, thus allowing the ventricles 28, 30, which are in diastole, to fill with blood. The impulse then continues to the bundle of His, which is a thick bundle of fibers extending down the septum wall 22, and spreads to the right and left bundle branches. The impulse continues from the right and left bundle branches to the Purkinje fibers, which spread throughout the inner surface of the right and left ventricles 28, 30.

Additional details about the heart and the cardiac conduction system may be found in the following publications: *Gray's Anatomy* by Henry Gray, F.R.S., published 1974 by Running Press, Philadelphia Pa.; *Dorland's Illustrated Medical Dictionary*, 25th Edition, published 1974 by W. B. Saunders, Philadelphia-London-Toronto; and *McGraw-Hill Encyclopedia of Science & Technology*, 6th Edition, Volume 3, pages 229 to 261. The entire disclosure of each of the above-identified references is incorporated herein by reference.

Cardiac conduction defects arise when the cardiac conduction system fails to sufficiently develop, control or transmit ionic current through the specialized cardiac cells of the heart. For example, bradycardia is a conduction defect that results in a slow or intermittently slow heartbeat. Bradycardia is considered clinically significant when the heart rate falls below about 60 beats per minute. Bradycardia may occur congenitally, or it may originate in the sinoatrial node, the atrioventricular node or the bundle of His.

Another type of cardiac conduction defect is tachycardia. In general, tachycardia is characterized by an excessively rapid heart rate. Tachycardia is considered clinically significant when the heart rate exceeds about 100 beats per minute. There are several forms of tachycardia, ranging in seriousness from inconvenient to life threatening. Some forms of tachycardia have origins in the upper cavities of the heart (supra ventricular tachycardia), while others originate from accessory pathways alongside the atrioventricular node (e.g. Wolf-Parkinson-White syndrome). Tachycardia may result in circus rhythms within the ventricle, and also uni-directional block phenomena within the atrioventricular node.

In general, atrial tachycardia is less serious because the remainder of the heart is usually unable to follow the very high triggering rhythms. Atrial tachycardia may be further mitigated because it is often accompanied by various degrees of atrioventricular block which reduces the ventricular rate to a more tolerable level. In any event, atrial tachycardia reduces cardiac output and causes shortness of breath, reduced stamina, and other ailments.

Ventricular tachycardia is characterized by severe reduction in the cardiac output and may result in periodic unconsciousness. There is also a significant potential for ventricular tachycardia to degrade to ventricular fibrillation with fatal results.

The currently used methods of treating cardiac conduction defects have focused primarily on treating the symptoms. Bradycardia is typically treated by providing electrical stimulation to the heart using an implanted or external pacemaker device. The pacemaker generally takes control of the triggering functions of the heart to increase the heart rate to a more normal level (about 70 beats per minute). Of course, the surgical procedure for connecting a pacemaker to the heart is invasive, and the pacemaker device requires periodic and expensive professional observation and maintenance. Atrial tachycardia is usually treated using drugs, surgery or an implantable pacemaker/cardioverter/defibrillator. These treatments have varying degrees of effectiveness, depending on the patient and the specific form of tachycardia. However, it is estimated that approximately 20% of all atrial tachycardia patients are refractory to the commonly used drug treatments. Ventricular tachycardia is typically treated with implantable cardioverters/defibrillators which have the same general drawbacks as pacemaker devices.

Thus, known methods of alleviating bradycardia and tachycardia conduction defects have focused primarily on prescribing treatments for the symptoms, rather than attacking the potential causes. Such causes have been ascribed to developing fibrosis, sequelae to myocardial infarction, ischemia and congestive heart failure, as well as some congenital causes. See, for example, *Disorders of Atrioventricular Conduction in Acute Myocardial Infarction*, Cardiology Clinics, Vol. 2, No. 1, February 1984, pages 29–34, by Jerry C. Griffin, M.D.; *Arrhythmias in Acute Myocardial Infarction*, Medical Clinics of North Americas Vol. 68 No. 4, July 1984, pages 1001–1008, by Galen S. Wagner, M.D.. However, these causes of cardiac conduction defect have not been discussed as reversible phenomena.

Thus, there is a need for a method of treating cardiac conduction defects that overcomes the expense, invasiveness, physical and psychological traumas, ineffectiveness, and other shortcomings of known methods of treatment.

Congestive heart failure occurs generally when significant regions of the heart becomes stiff and inflexible such that it looses some of its ability to properly contract, thereby reducing the cardiac output to clinically significant levels. Congestive heart failure has been generally attributed to a number of conditions such as heart valve malfunction. However, there is no obvious cause of congestive heart failure. Thus, there is a need for a method of treating congestive heart failure.

It is hereby noted that the descriptions of the art provided in this disclosure are not intended to constitute an admission that any patent, publication or other information referred to herein qualifies as "prior art" within the meaning of 35 § 102. Also, in accord with 37 CFR § 1.97, these descriptions shall not be construed to mean that: 1) a search has been made; 2) Applicant(s) consider(s) the information discussed herein to be "material" as defined in 37 CFR § 1.97; or 3) no other material information exists.

SUMMARY OF THE INVENTION

Thus, it is an object of the present invention to provide improved methods and devices for treating cardiac conduction defects.

It is another object of the present invention to provide improved methods and devices for treating acquired bradycardia conduction defects.

It is another object of the present invention to provide improved methods and devices for treating acquired tachycardia conduction defects.

It is another object of the present invention to provide a low cost acute interventional approach to correcting cardiac conduction defects.

It is a further object of the present invention to provide methods and devices for treating congestive heart failure.

These and other objects are achieved in accordance with the present invention by providing a method of treating bradycardia or tachycardia conduction defects in the heart by intervention in any occluded coronary arteries that feed blood to the specialized cardiac conduction cells of the heart. There is also provided a method of treating congestive heart failure by intervention in any occluded coronary arteries that feed blood to the ischemic regions of the heart. In either situation, means for dilating the occlusion is applied to the affected arteries, thereby establishing increased blood flow to the ischemic regions of heart, or to the specialized cardiac conduction cells of the heart.

For example, a patient who has been diagnosed with clinically significant acquired bradycardia (heartbeat below 60 beats per minute) is evaluated via conventional medical procedures to determine whether there are any occlusions in the coronary arteries that feed blood to the specialized cardiac conduction cells of the heart. The patient is found to have occlusions in the sinoatrial nodal artery which feeds the sinoatrial node and originates in either the right coronary artery or the circumflex branch of the left coronary artery. It is determined that the sinoatrial nodal artery for this patient originates in the circumflex branch of the left coronary artery. A small diameter catheter device, such as a balloon dilation catheter having an OD less than 1½ mm, is routed through the patient's vascular system to the occluded portion of the sinoatrial nodal artery using conventional Percutaneous Transluminal Coronary Angioplasty (PTCA) techniques. The catheter's balloon is positioned across the occlusion and inflated to open a passage through the vessel and allow increased blood flow to the sinoatrial node.

The means for dilating the occlusion may take a variety of forms. As noted above, the occlusion may be opened using a conventional dilation balloon catheter. The occlusion may also be opened by using an atherectomy device, applying drug treatments via a drug delivery catheter, inserting a stent in the artery, or a wire, or using other traditional angioplasty devices and methods. Such traditional angioplasty devices and methods have not, prior to the present invention, been used in the coronary artery branches that feed blood directly to the specialized conduction nodes of the heart, for this purpose.

Accordingly, the present invention achieves several advantages. For example, the present invention may be implemented using conventional PTCA which involves considerably less traumatic surgical procedures than pacemakers, defibrillators, cardioverters, and other such devices. The present invention also involves lower overall costs and considerably less post-surgical monitoring than pacemakers, defibrillators, cardioverters, and other such devices. Thus, the present invention avoids the risks associated with the above-identified implantable devices which may malfunction or require protracted monitoring and periodic refurbishment. Also, the present invention is directed at alleviating the causes of the cardiac conduction defects instead of merely treating the symptoms. Accordingly, it is expected that the present invention will have a more permanent effect than the known methods which treat the symptoms of cardiac conduction defects.

BRIEF DESCRIPTION OF THE DRAWINGS

FIG. 13 illustrates a general catheter device that has been routed through a patient's vascular system to an occlusion in the sinoatrial nodal branch of the right coronary artery.

DETAILED DESCRIPTION OF THE PREFERRED EMBODIMENTS

Figure 1:
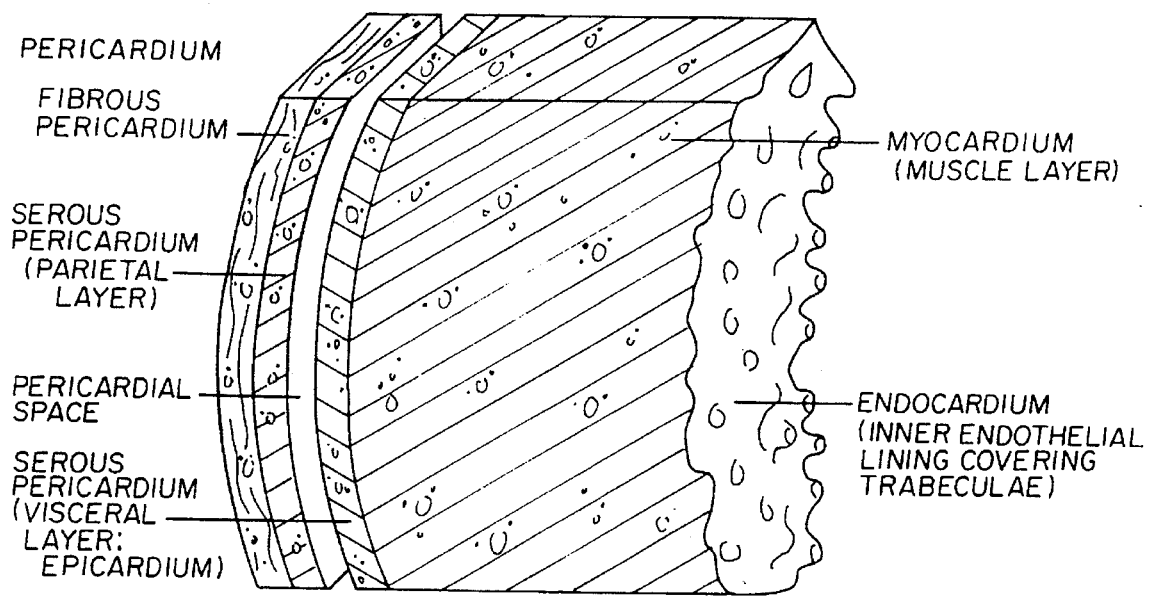
FIG. 1 is a sectional view illustrating a portion of the wall of a human heart.
Figure 2:
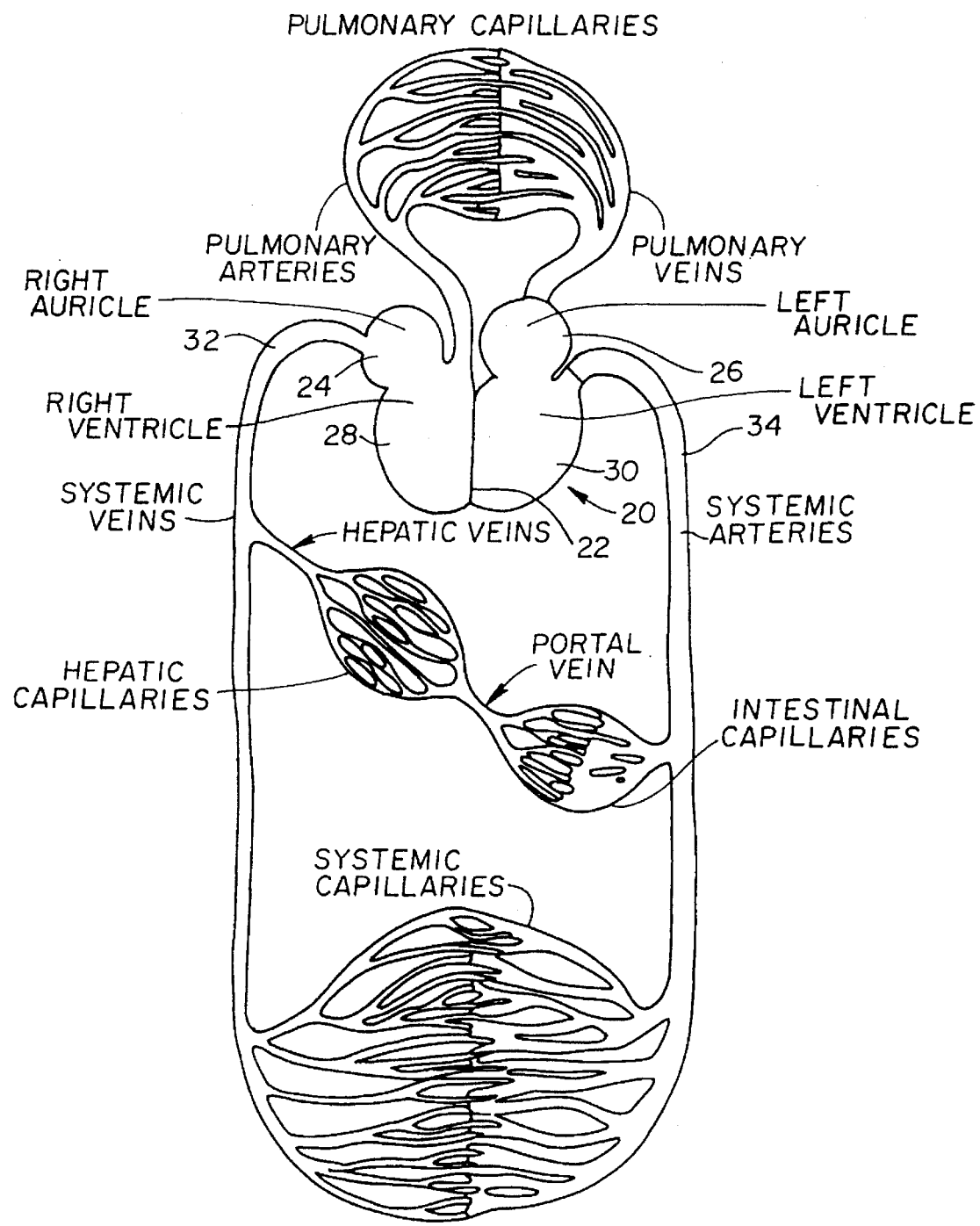
FIG. 2 is diagram of the human blood circulation system.
Figure 3:
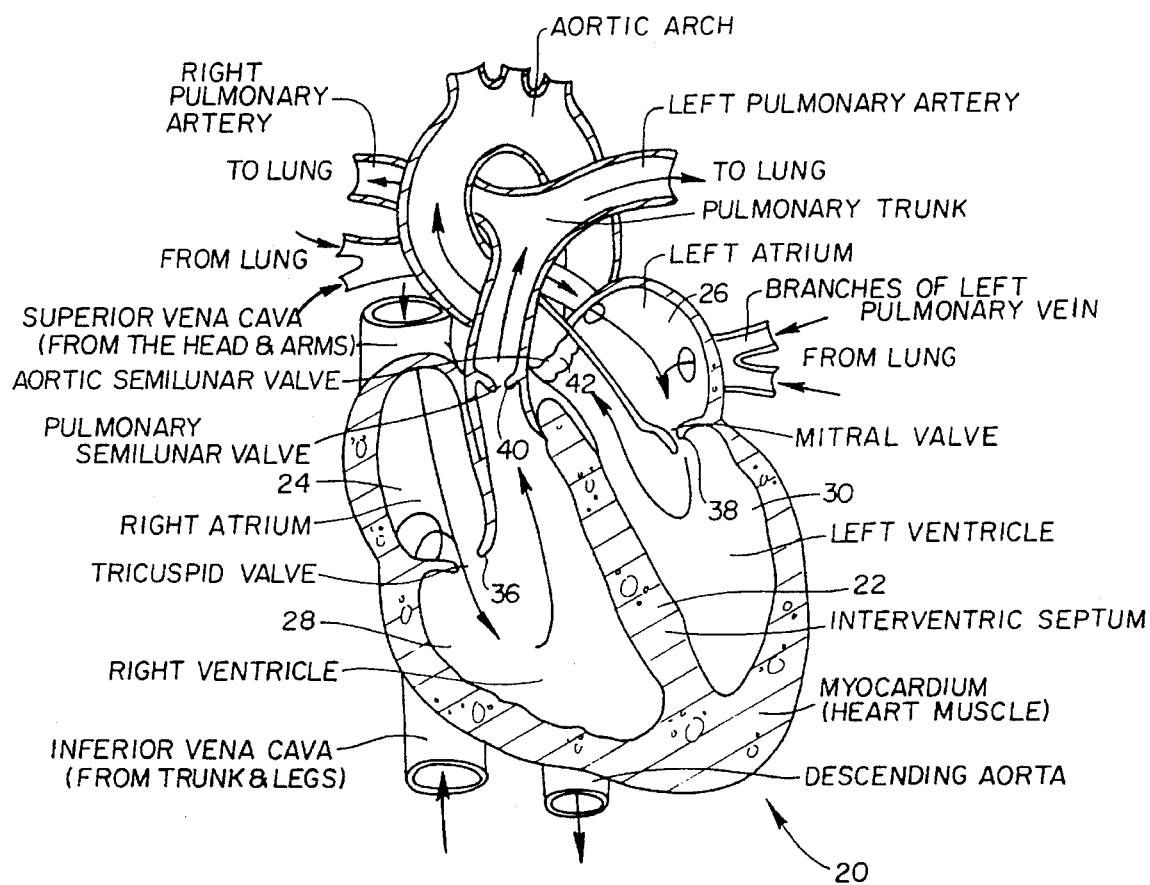
FIG. 3 is a diagram of a human heart.
Figure 4:
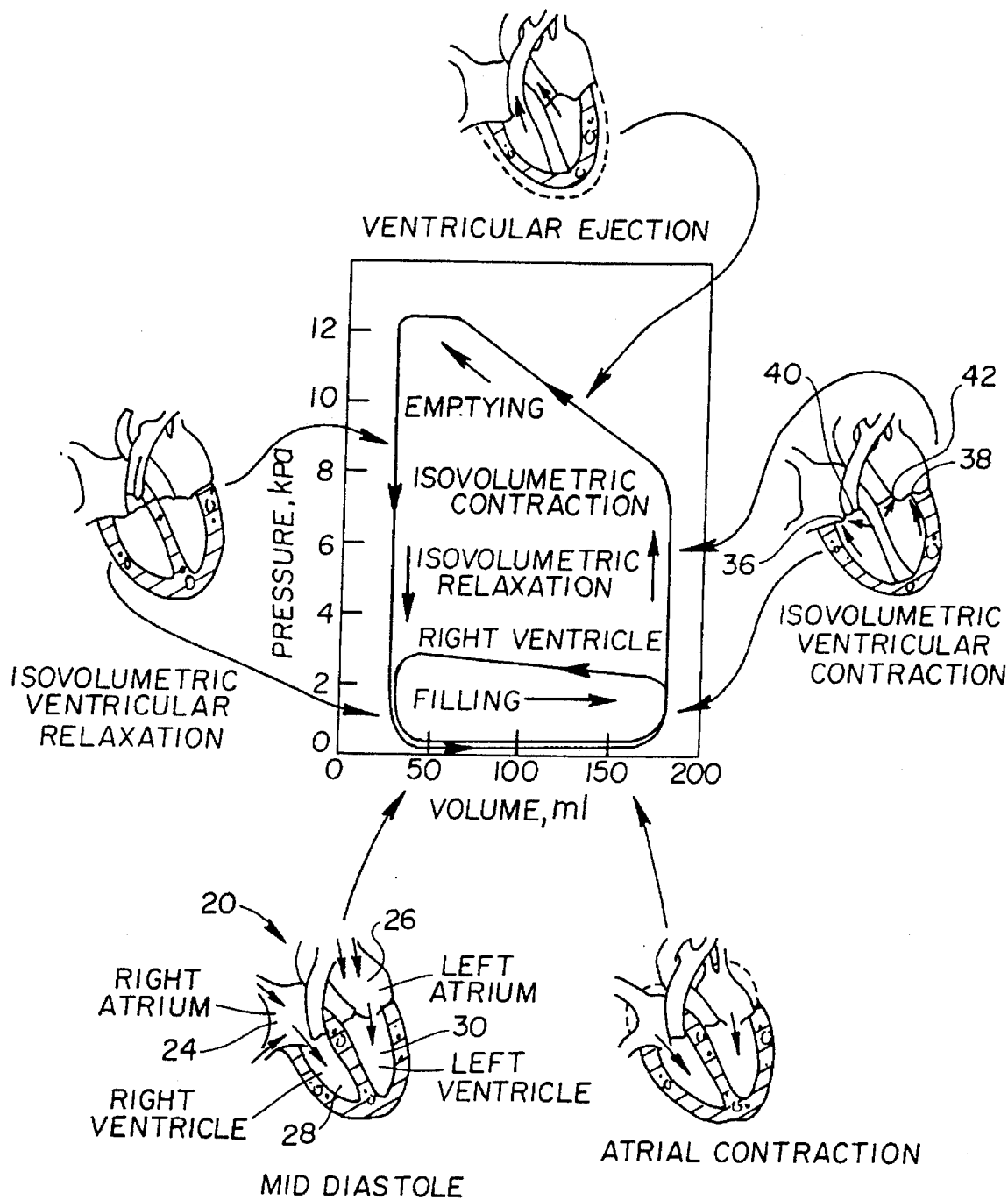
FIG. 4 is a diagram illustrating the four phases of the cardiac cycle of a human heart.
Figure 5:
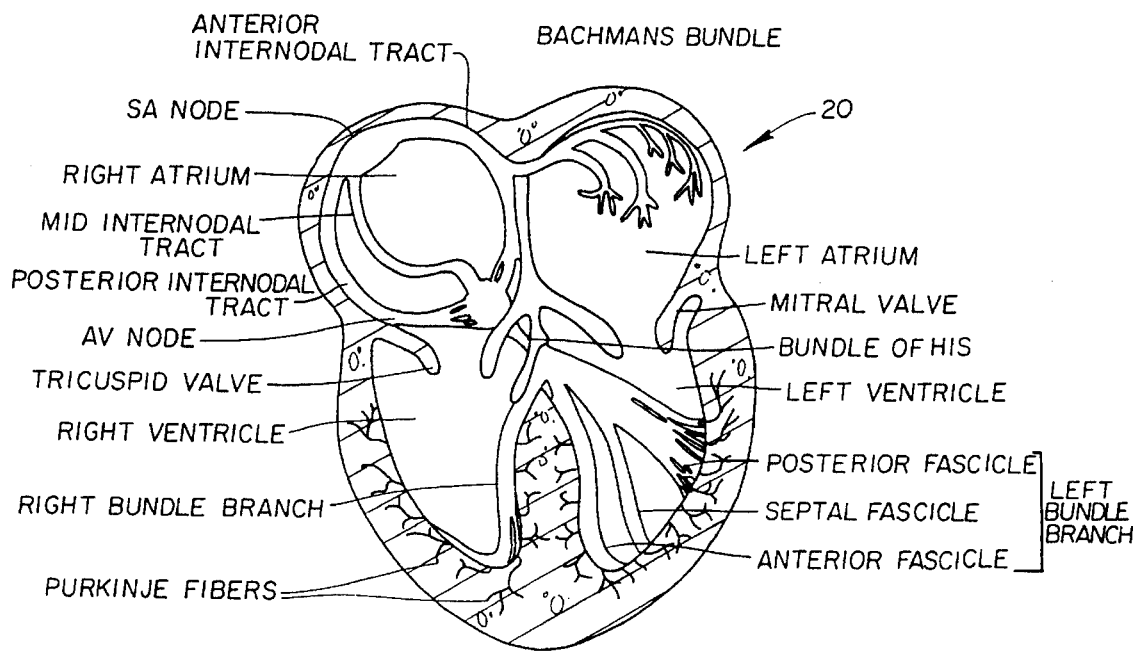
FIG. 5 is a diagram illustrating the specialized conduction nodes and fibers of the human heart.
Figure 6:
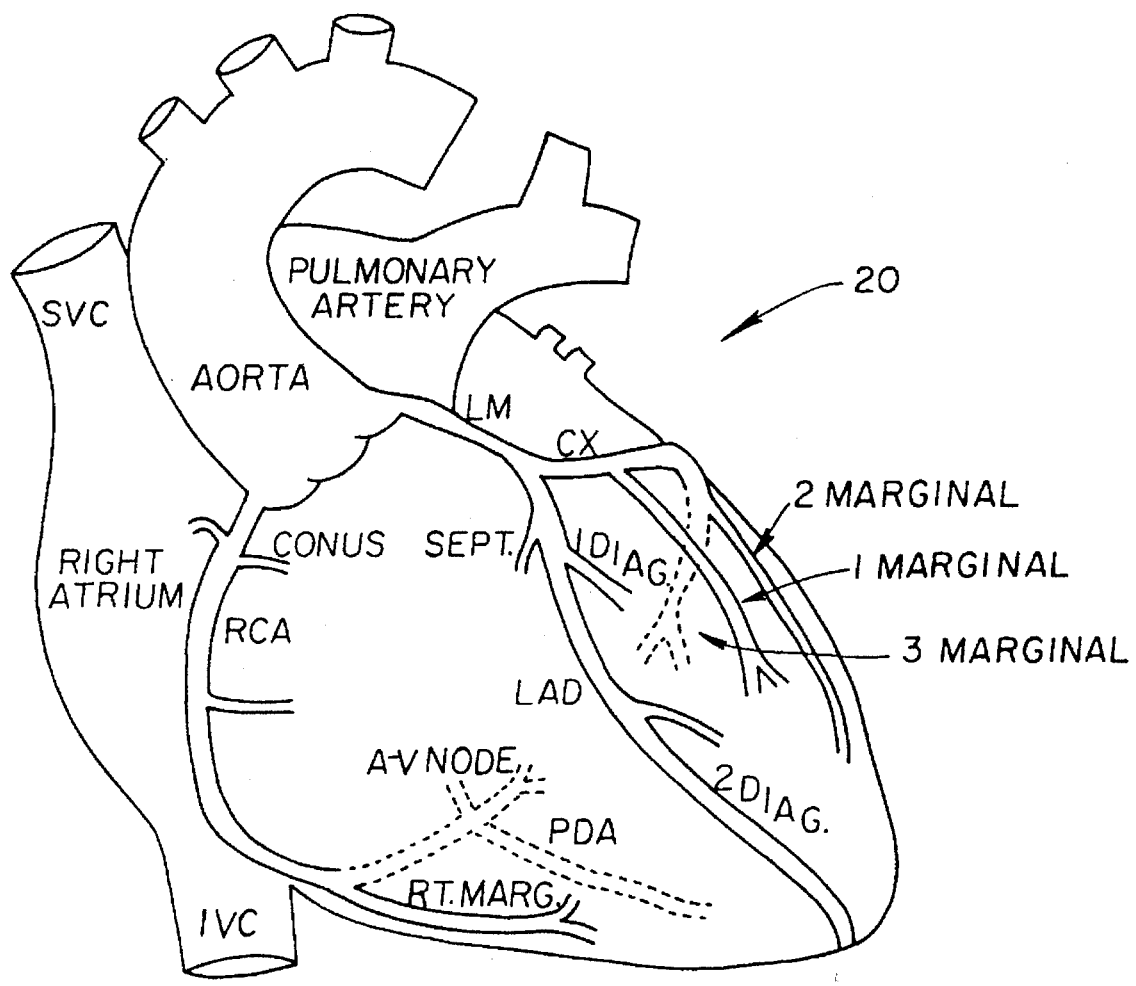
FIG. 6 is a diagram illustrating the coronary arteries and their branches against the heart.
Figure 7:
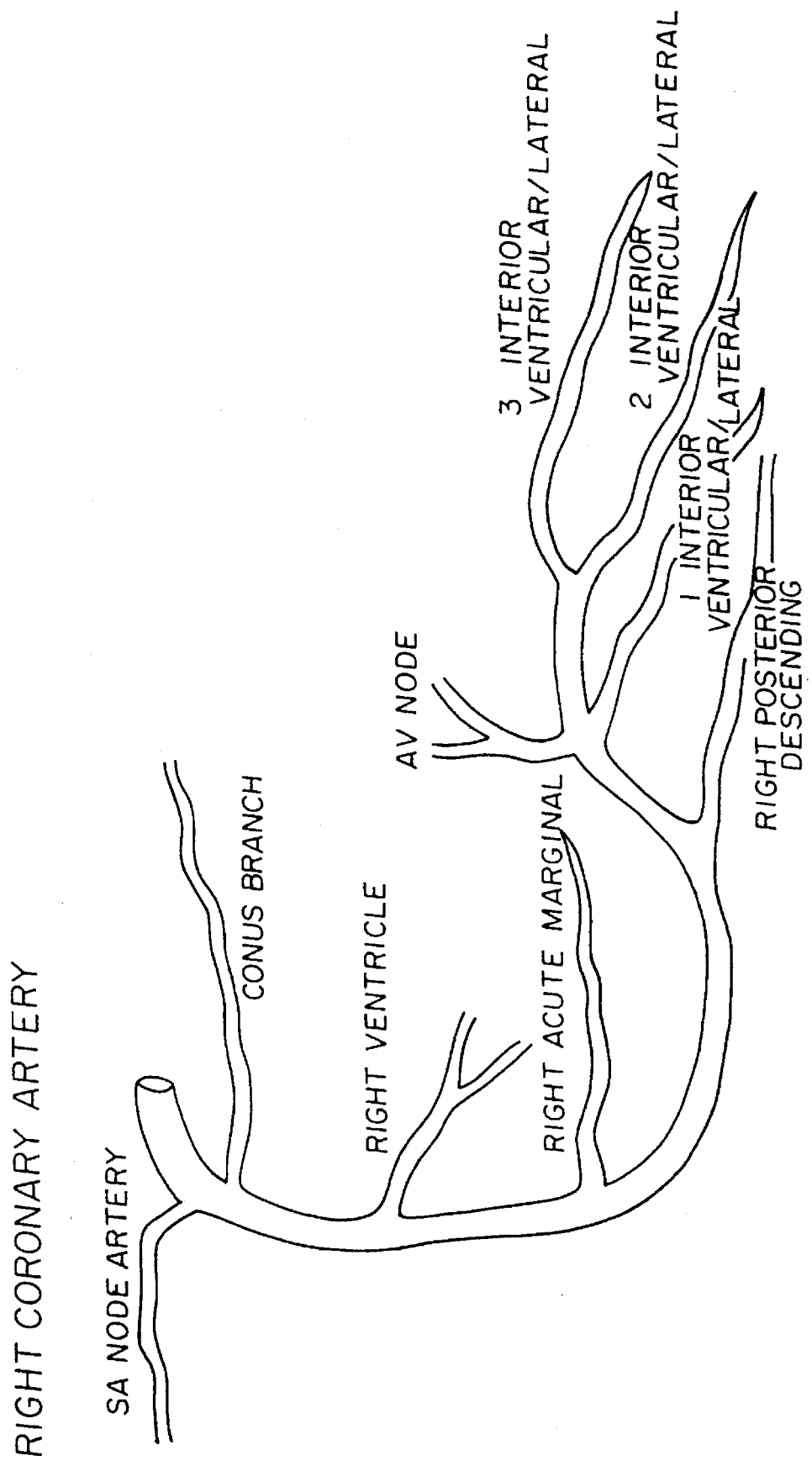
FIG. 7 illustrates the right coronary artery and its branches.
Figure 8:
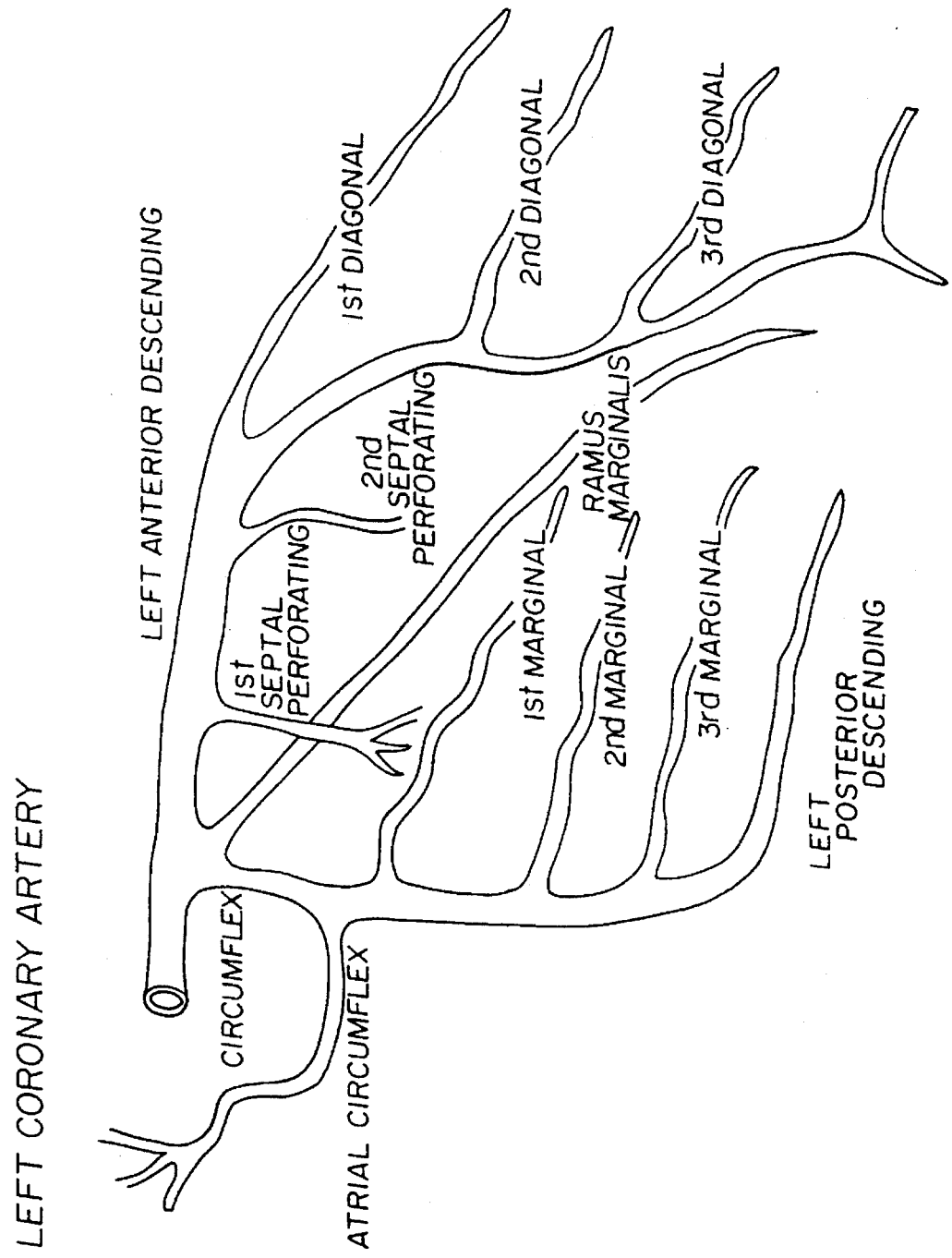
FIG. 8 illustrates the left coronary artery and its branches.

FIGS. 6, 7 and 8 generally illustrate the coronary arteries and their branches. In general, the arteries are cylindrical tubular vessels that convey blood from the ventricles of the heart to every part of the body. The common trunk of the systemic arteries is formed by the aorta which commences at the left ventricle of the heart. The arteries are found in nearly every part of the body, with the exception of the hairs, nails, epidermis, cartilages, and cornea. The larger trunks of the arteries usually occupy protected regions of the body where they are less exposed to injury.

The aorta commences at the upper part of the left ventricle, where it is about 1⅛ inches in diameter. After ascending for a short distance, the aorta arches backward and toward the left side of the heart. Thus, the aorta is initially divided into the ascending aorta, the arch of the aorta, and the descending aorta.

The first two branches off the ascending aorta are the right and left coronary arteries, shown in detail in FIGS. 7 and 8. Because the heart is a muscular organ, it also requires a blood supply. Blood is supplied to the heart muscle via the right and left coronary arteries which lie on the surface of the heart muscle (see FIG. 6) and supply the heart with the blood it requires.

As shown in FIG. 7, the right coronary artery consists of one major artery with several side branches, such as the right ventricular, acute marginal, conus, sinoatrial nodal, posterior descending, atrioventricular nodal and inferior lateral branches.

As shown in FIG. 8, the left coronary artery consists of two major artery branches. The most proximal portion of the left coronary artery is known as the left main. The left main then bifurcates into two major arterial branches—the circumflex and the left anterior descending. The dominant branch of the circumflex is the marginals. However, in a person who is left dominant, the posterior descending artery originates from the circumflex instead of the right coronary artery. The diagonals and the septal perforators originate off the left anterior descending artery.

Congestive heart failure occurs generally when significant regions of the heart becomes stiff and inflexible such that it looses some of its ability to properly contract, thereby reducing the cardiac output to clinically significant levels. Congestive heart failure has been generally attributed to a number of conditions such as heart valve malfunction.

Cardiac conduction defects arise when the cardiac conduction system fails to sufficiently develop, control or transmit ionic current through the specialized cardiac cells of the heart. For example, bradycardia is a conduction defect that results in a slow or intermittently slow heartbeat. Bradycardia is considered clinically significant when the heart rate falls below about 60 beats per minute. Bradycardia may occur congenitally, or it may originate in the sinoatrial node, the atrioventricular node or the bundle of His.

Another type of cardiac conduction defect is tachycardia. In general, tachycardia is characterized by an excessively rapid heart rate. Tachycardia is considered clinically significant when the heart rate exceeds about 100 beats per minute. There are several forms of tachycardia, ranging in seriousness from inconvenient to life threatening. Some forms of tachycardia have origins in the upper cavities of the heart (supra ventricular tachycardia), while others originate from accessory pathways alongside the atrioventricular node (e.g. Wolf-Parkinson-White syndrome). Tachycardia may result in circus rhythms within the ventricle, and also uni-directional block phenomenon within the atrioventricular node.

In general, atrial tachycardia is less serious because the remainder of the heart is usually unable to follow the very high triggering rhythms. Atrial tachycardia may be further mitigated because it is often accompanied by various degrees of atrioventricular block which reduces the ventricular rate to a more tolerable level. In any event, atrial tachycardia reduces cardiac output and causes shortness of breath, reduced stamina, and other ailments.

Ventricular tachycardia is characterized by severe reduction in the cardiac output and may result in periodic unconsciousness. There is also a significant potential for ventricular tachycardia to degrade to ventricular fibrillation with fatal results.

The present invention provides a method of treating congestive heart failure and cardiac conduction defects (such as bradycardia or tachycardia) by intervention in any occluded coronary arteries that feed blood to ischemic regions of the heart, or to the specialized cardiac conduction cells of the heart. Means for dilating the occlusion is applied to the affected arteries, thereby establishing increased blood flow to the ischemic regions and/or specialized cardiac conduction cells of the heart.

Figure 9:
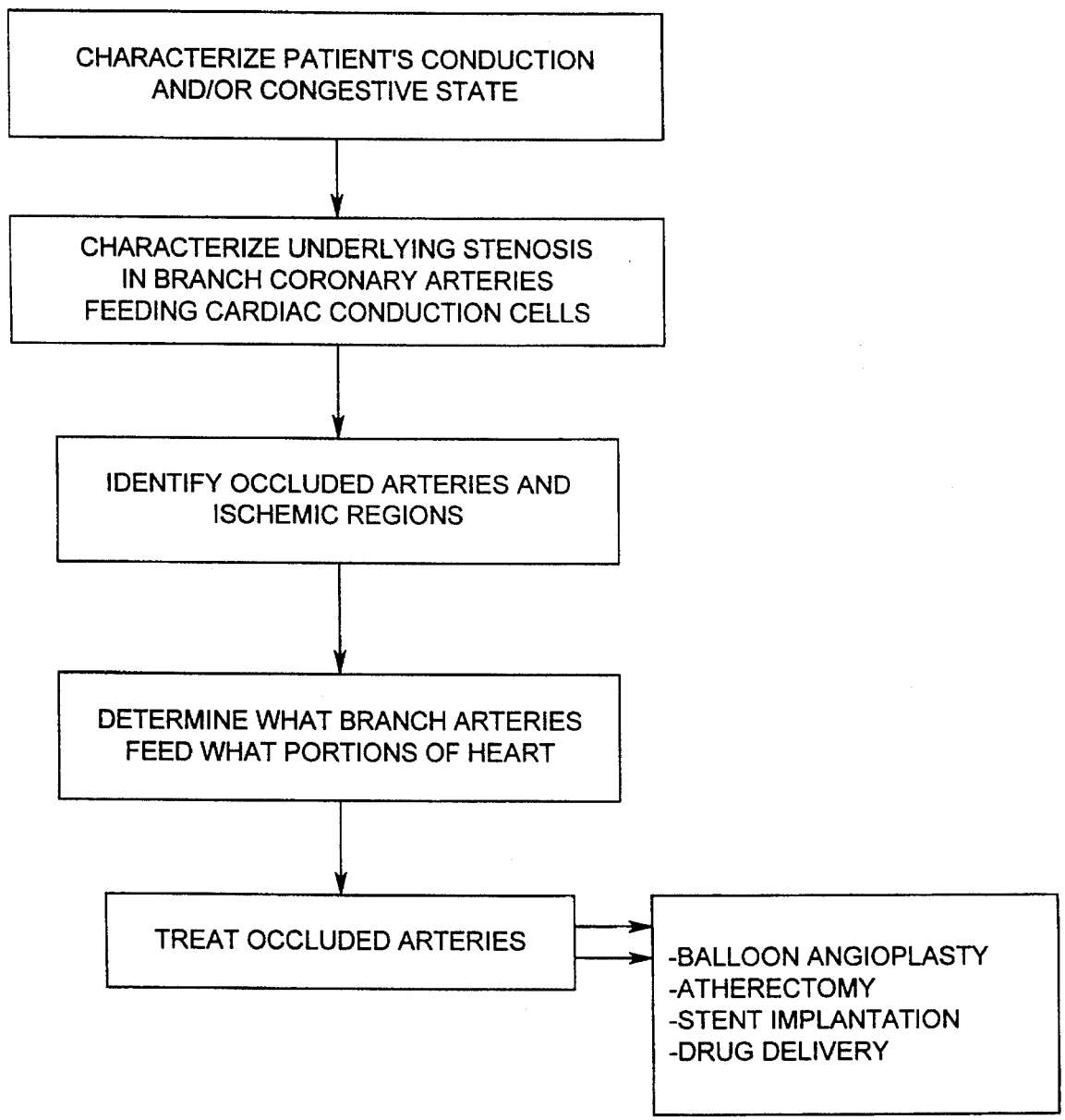
FIG. 9 is a flow diagram illustrating the steps of a method embodying a preferred embodiment of the present invention.

FIG. 9 is a flow diagram illustrating the general steps of a method embodying the present invention. First, a combination of surface EKGs, diagnostic catheter procedures, and electro-physiologic studies are used to characterize the patient's conduction state, locate any ischemic regions of the heart, and characterize the underlying occlusion(s) in the coronary arteries which are the cause of the aberrations. Locating ischemic regions may also require an EP study with endocardial stimulating catheters. The patient is then diagnosed for any clinically significant cardiac conduction defects or congestive heart disease. The present invention has particular application to patients having conduction defects with the origins in the sinoatrial node, the atrioventricular node or in the more distal components of the conduction system (e.g., bradycardia). The present invention also has application to patient's having conduction defects with origins in the myocardial layer of the atria or ventricles (e.g., tachycardia, or congestive disease).

The patient's coronary arteries are then evaluated, using conventional diagnostic catheterization techniques, to determine whether there are any occlusions in the coronary branch arteries that feed blood directly to the specialized cardiac conduction cells of the heart. In particular, the patient should be assessed for the possibility of stenoses or occlusions in the left anterior descending artery or the right coronary artery, and in the specialized sinoatrial nodal artery, the atrioventricular nodal artery and the septal perforating branch of the left anterior descending artery. The patient is also evaluated to determine whether there are any ischemic muscle regions in the atrium or ventricle walls of the heart. Ischemia is generally defined as localized tissue anemia due to obstruction of the inflow of arterial blood.

The patient's coronary artery branches are further evaluated to determine what branch arteries feed blood to what portions of the heart. This is important because the general connections between these arteries and the heart may vary from person to person. The sinoatrial node, which is the initial triggering source for the electrical impulses of the heart, is fed by the sinoatrial nodal artery. The sinoatrial nodal artery is a side branch of the right coronary artery in about 50% of the people, and a side branch of the left circumflex in the other 50%. Blood flow to the sinoatrial node can also be affected by more proximal occlusions in the left circumflex or right coronary artery. Opening occlusions in these arteries will also increase the flow of blood to the sinoatrial node.

The atrioventricular node is supplied almost exclusively by the atrioventricular nodal artery. In 90% of all people the atrioventricular nodal artery arises from the right coronary artery. Occlusion of the atrioventricular nodal artery is frequently associated with atrioventricular block at the level of the atrioventricular node. In contrast, the blood supply of the more distal components of the specialized cardiac conduction system is more varied. For example, it has been found that in 9 of 10 people the bundle of His has a dual blood supply. It has also been found that in 5 of 10 people the proximal right bundle branch also has a dual blood supply. Additionally, the proximal right bundle branch extends from the septal branch of the left anterior descending artery in only 4 of 10 people, and from the atrioventricular nodal artery in only 1 of 10 people. Thus, a variety of combinations of bundle branch block may occur after occlusion of either the left anterior descending or right coronary arteries, depending upon the underlying vascular distribution to the various elements of the conduction system.

After the arterial connections to the heart are determined, the final step is to treat the occluded arteries and/or the ischemic regions of the heart. A variety of known PTCA related procedures may be used, including balloon angioplasty, atherectomy, stent-implantation, drug delivery, and others. Prior to the present invention, such PTCA procedures have not been used to intervene in the branch coronary arteries that feed blood directly to the specialized cardiac conduction cells of the heart (including ischemic regions). Examples of PTCA devices and techniques are disclosed in the following U.S. Pat. Nos.: 4,838,269 entitled "Manifold for Angioplasty Balloon Catheter"; 4,838,268 entitled "Non-over-the Wire Balloon Catheter"; 4,846,174 entitled "Angioplasty Dilating Guide Wire"; 4,930,341 entitled "Method of Prepping a Dilatation Catheter"; 4,944,745 entitled "Perfusion Balloon Catheter"; 4,976,690 entitled "Variable Stiffness Angioplasty Catheter"; 5,011,537 entitled "Pressure Gauge Cleaning Method"; 5,019,041 entitled "Balloon Catheter Inflation Device"; 5,032,113 entitled "Innerless Catheter"; 5,035,705 entitled "Method of Purging A Balloon Catheter"; 5,047,045 entitled "Multi-section Coaxial Angioplasty Catheter"; 5,085,636 entitled "Balloon Catheter With Inflation-deflation Valve"; 5,129,887 entitled "Adjustable Manifold For Dilatation Catheter"; 5,147,300 entitled "Balloon Catheter Inflation Device"; 5,156,594 entitled "Balloon Catheter With Distal Guide Wire Lumen"; 5,156,595 entitled "Dilatation Balloon Catheter And Method of Manufacture"; 5,085,662 entitled "Atherectomy Catheter and Related Components"; and 5,100,381 entitled "Angioplasty Catheter." The entire disclosures of the above-identified patents are incorporated herein by reference.

The following is an example of how the method of the present invention may be used to treat a patient for cardiac conduction defects. A patient who has been diagnosed with clinically significant acquired bradycardia (heartbeat below 60 beats per minute) is evaluated via conventional medical procedures to determine whether there are any occlusions in the coronary arteries that feed blood to the specialized cardiac conduction cells of the heart. The patient is found to have occlusions in the sinoatrial nodal artery which feeds the sinoatrial node and originates in either the right coronary artery or the circumflex branch of the left coronary artery. It is determined that the sinoatrial nodal artery for this patient originates in the right coronary artery.

Figure 12:
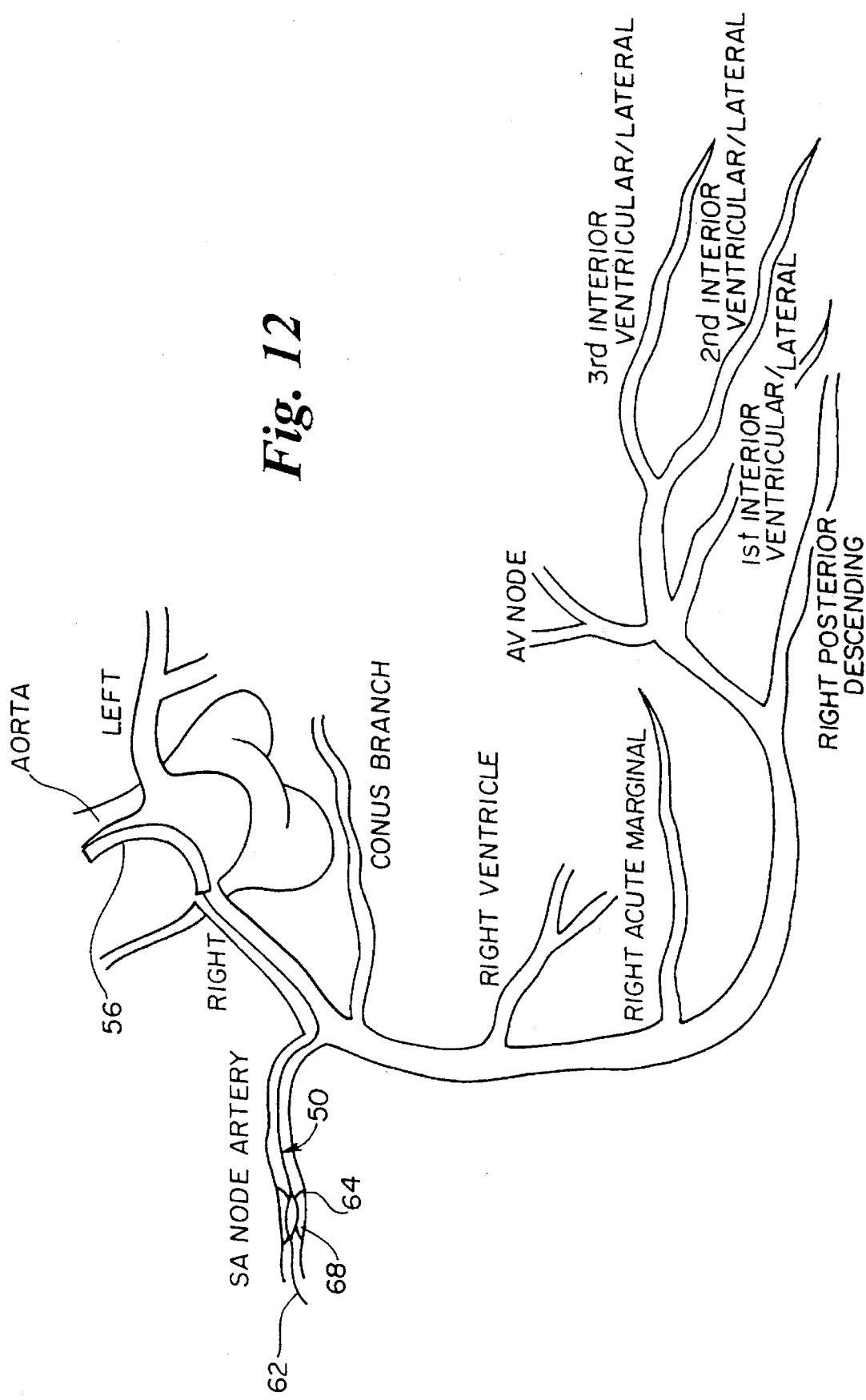
FIG. 12 illustrates a balloon catheter device that has been routed through a patient's vascular system to an occlusion in the sinoatrial nodal branch of the right coronary artery.

As illustrated in FIG. 12, a small diameter catheter device, such as a balloon dilation catheter 50, is routed through the patient's vascular system to the occluded section of the sinoatrial nodal artery using conventional Percutaneous Transluminal Coronary Angioplasty (PTCA) techniques. The general objective of PTCA is to open occlusions caused by lesions within a vessel.

Figure 10:
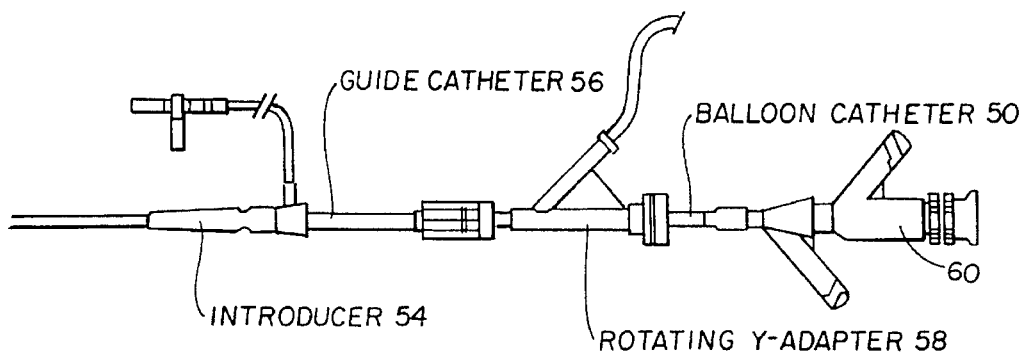
FIG. 10 illustrates a configuration of PTCA devices that may be used in connection with implementing the method of the present invention.

FIG. 10 illustrates several components used in PTCA to introduce the balloon catheter 50. First, the femoral artery is entered percutaneously and an introducer sheath 54 is inserted into the femoral artery to provide access to the patient's vasculature. A guiding catheter 56 is introduced over a guide wire (not shown) into the sheath 54 and advanced up to the aortic arch. The guide wire is then removed. A Y-adapter 58 and manifold assembly 60 are attached to the guiding catheter 56 for dye delivery, flushing capabilities and arterial pressure monitoring. The guiding catheter 56 is advanced and maneuvered until it is properly engaged in the ostium of the right coronary.

Another guide wire 62 (shown in FIG. 12) and a balloon dilatation catheter 50 are inserted into the guiding catheter 56 through the Y-adapter 58. A bolus of intraarterial heparin, usually 10,000 units, is administered for anticoagulation purposes. Additional heparin is given every 1 to 1 and ½ minutes during the procedure, or more frequently if needed. Sublingual or IV nitroglycerin and nifedipine may be given to reduce the potential for coronary spasm.

A slight rotation of the distal tip of the guide catheter 56 helps the coaxial introduction of the guide wire 62 into the right coronary artery and the sinoatrial nodal branch thereof. The guide wire 62 is then advanced into the most distal portion of the sinoatrial nodal artery in order to stabilize the system for advancement of the balloon catheter 50. The balloon catheter 50 is then tracked over the guide wire 62, and the balloon portion 64 of the balloon catheter 50 is centered on the lesion 68 (FIG. 12). Once properly positioned, the balloon 64 is inflated with a $^{50}/_{50}$ mixture of contrast fluid and normal saline. The balloon 64 is inflated anywhere from 15 seconds to a minute, or longer, depending on the patient's tolerance.

Depending on the hardness of the lesion 68, multiple inflations may be necessary. Each inflation is usually assessed by injecting the sinoatrial artery with small amounts of dye. When the lesion 68 is assessed as sufficiently dilated, the balloon 64 is deflated, and the balloon catheter 50 is pulled back into the guide catheter 56 and contrast is injected to further enhance angiographic assessment of the lesion 68. The guide wire 62 is generally left across the lesion 68 for approximately 15 minutes in case it becomes necessary to again dilate the lesion 68.

The above procedure is described in connection with an "over-the-wire" or "rail" system which provides a separate lumen in the catheter for accommodating the guide wire. The procedure may also be implemented with a "fixed wire" system which attaches the guide wire permanently to the tip end of the catheter, thereby eliminating the need for a guide wire lumen in the catheter and providing a lower profile device. If the vessel of interest is particularly small, a fixed-wire device might be a preferred alternative.

Once the patient is stable, the entire balloon dilatation system is removed and post dilation cine angiograms are performed. All views are checked to determine flow and patency of the dilated artery. The EKG is monitored, and the patient's conduction state is again examined for normalcy.

Although the above example was directed to the sinoatrial node, other portions of the nodal/fiber connections of the heart may be similarly treated. Additionally, because arterial occlusion can be the cause of congestive heart failure, a similar method may be used to treat congestive heart failure.

Figure 11:
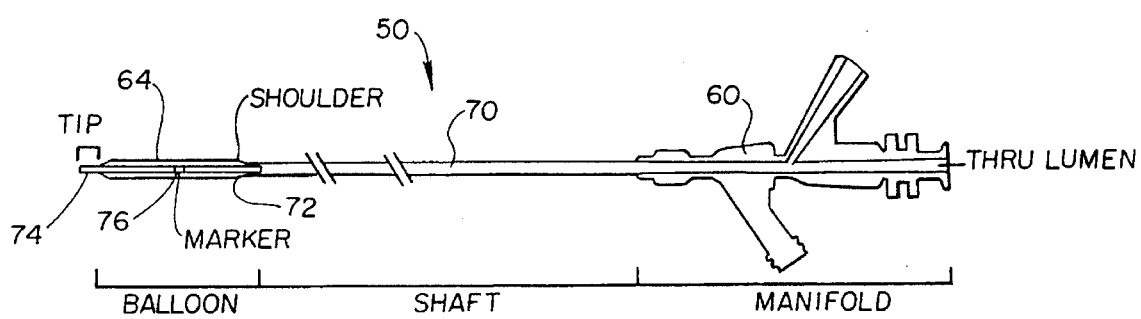
FIG. 11 illustrates the general features of a balloon catheter that may be used in connection with implementing the method of the present invention.

The details of the balloon catheter 50 are illustrated in FIG. 11. The balloon catheter 50 is shown inserted through a manifold 60. The balloon catheter 50 generally includes a proximal shaft portion 70, a balloon portion 64, a shoulder 72 for interfacing the shaft 70 to the balloon 64, a balloon tip 74 at the distal end of the balloon 64, and a radiopaque marker 76 for viewing the position of the balloon 64 within the vasculature by angiographic procedures.

The outer diameter (OD) of the balloon catheter 50 must be extremely small in order to maneuver it through the small coronary artery branches that feed blood to the specialized cardiac conduction cells of the heart. These branch arteries range in size from about 1 mm to about 1 and ½ mm. Accordingly, the deflated OD of the balloon catheter 50 should range in size from 1 and ½ mm down to preferably about 0.5 millimeters.

The balloon catheter 50 may be replaced with other catheter devices for treating and dilating occlusions. Such a catheter is represented diagrammatically at 80 in FIG. 13. In one instance, the catheter 80 may be a motor-driven atherectomy catheter which could be used to cut, abrade, or otherwise open a passage through the obstruction. The atherectomy catheter would have the same general size constraints as noted above for the dilatation balloon catheter 50. U.S. Pat. No. 4,936,845 discloses a catheter having a motor-driven rotating head at its distal end for boring a passageway through an obstructed blood vessel. U.S. Pat. No. 4,854,325 discloses a guide wire that is motor driven through a ramming back-and-forth action to assist in forming a pilot passageway through the obstruction. Similar devices are disclosed in U.S. Pat. Nos. 5,007,917; 5,011,490; 5,030,201; and 5,059,203. The entire disclosure of each of these patents is incorporated herein by reference.

The catheter 80 may also be a stent-implanting catheter. A stent-implanting catheter is used to implant a stent in a formerly occluded vessel after it has been opened. The stent provides additional support to the affected region of the vessel. Stents are typically hollow tubular devices which have sufficient rigidity to maintain the diameter of the vessel, while at the same time allowing blood to pass. Examples of implanted stents are shown in the following U.S. Pat. Nos.: 4,913,141; 4,876,906; 4,856,516; and 4,820,298. The entire disclosure of the above patents are incorporated by reference.

The catheter 80 may also be a drug-delivery catheter. Drug-delivery catheters typically provide a lumen for allowing the infusion of active agents such a heparin, thrombolytics, or other chemical agents. These agents may act on the occlusion itself, or be supplied directly to any ischemic regions of the heart. The drug-delivery catheter may be incorporated into a conventional balloon catheter by providing a separate lumen for delivering chemical agents. The drug-delivery catheter has the same size constraints as described above for the balloon dilatation catheter.

Another method of delivering drugs to a specific vascular site is the use of a perforated or weeping balloon. An example of such is disclosed in U.S. Pat. No. 5,087,244. Also, U.S. patent application Ser. No. 07/740,047, filed Aug. 2, 1991, and assigned to the assignee of this application, discloses a drug delivery catheter. The entire disclosure of both of these documents are incorporated herein by reference.

Thus, it can be seen from the above detailed description that the present invention achieves several advantages. For example, the present invention may be implemented using conventional PTCA which involves considerably less traumatic surgical procedures than pacemakers, defibrillators, cardioverters, and other such devices. The present invention also involves lower overall costs and considerably less post-surgical monitoring than pacemakers, defibrillators, cardioverters, and other such devices. Thus, the present invention avoids the risks associated with the above-identified implantable devices which may malfunction or require protracted monitoring and periodic refurbishment. Also, the present invention is directed at alleviating the causes of the cardiac conduction defects instead of merely treating the symptoms. Accordingly, it is expected that the present invention will have a more permanent effect than the known methods that treat the symptoms of cardiac conduction defects. Similar considerations also apply to the treatment of congestive heart failure.

While the above described embodiments of the invention are preferred, there are various modifications of structure, arrangement, composition and the like which do not part from the true scope of the invention. The scope of the invention is defined by the appended claims, and all devices and/or methods that fall within the meaning of the claims, either literally or by equivalents, are intended to be embraced therein.

I claim:

1. A method of treating cardiac conduction defects, the steps comprising:

diagnosing a cardiac conduction defect in a patient;

identifying a location of the cardiac conduction defect;

identifying at least one occluded artery from among the coronary arteries that deliver oxygenated blood to the location of the cardiac conduction defect;

subsequent to identifying said occluded artery, providing a first therapy for the cardiac conduction defect wherein the first therapy includes treating the occlusion in said occluded artery to permit increased blood flow through said occluded artery to the location of the cardiac conduction defect; and evaluating the patient's cardiac conduction status to determine whether the cardiac conduction defect has been reduced.

2. The method of claim 1 wherein said occluded artery feeds directly to the sinoatrial node.

3. The method of claim 2 wherein said occluded artery comprises the sinoatrial nodal artery.

4. The method of claim 1 wherein said occluded artery feeds directly to the atrioventricular node.

5. The method of claim 4 wherein said occluded artery comprises the atrioventricular nodal artery.

6. The method of claim 1 wherein said occluded artery feeds directly to ischemic regions of the heart.

7. The method of claim 6 wherein said ischemic regions are responsible for the presence of a tachycardia condition.

8. The method of claim 6 further comprising the step of delivering a chemical agent to said ischemic regions of the heart.

9. The method of claim 1 wherein said occlusion is treated by inflating a balloon across the occlusion.

10. The method of claim 1 wherein said occlusion is treated by cutting away at least part of the occlusion.

11. The method defined in claim 1 further comprising the step of delivering a drug to the site of occlusion.

12. A method of treating cardiac conduction defects, the steps comprising:

diagnosing a cardiac conduction defect in a patient;

identifying a location of the cardiac conduction defect;

identifying at least one occluded artery from among the coronary arteries that deliver oxygenated blood to the location of the cardiac conduction defect;

subsequent to identifying said occluded artery, providing a first therapy for the cardiac conduction defect wherein the first therapy includes inserting a catheter into a patient's vascular system; routing said catheter to an occlusion in a coronary artery that delivers oxygenated blood to the location of the cardiac conduction defect; using said catheter to at least partially open said occlusion, thereby increasing blood flow to the location of the cardiac conduction defect; and evaluating the patient's cardiac conduction status to determine whether any cardiac conduction defects have been reduced.

13. The method of claim 12 wherein said catheter comprises a balloon catheter.

14. The method of claim 12 wherein said catheter comprises an atherectomy catheter.

15. The method of claim 12 wherein said cardiac conduction defects comprise bradycardia.

16. The method of claim 12 wherein said cardiac conduction defects comprise tachycardia and fibrillation.

17. The method of claim 12 wherein said specialized cardiac cells comprise the sinoatrial node of the heart.

18. The method of claim 12 wherein said specialized cardiac cells comprise the atrioventricular node of the heart.

19. The method of claim 12 wherein said specialized cardiac cells comprise the His bundle of the heart.

20. The method of claim 12 wherein said specialized cardiac cells comprise the internodal tract of the heart.

21. The method of claim 12 wherein said specialized cardiac cells comprise the Bachman's Bundle fibers of the heart.

22. The method of claim 12 wherein said specialized cardiac cells comprise the left bundle branch of the heart.

23. The method of claim 12 wherein said specialized cardiac cells comprise the right bundle branch of the heart.

24. The method of claim 12 wherein said specialized cardiac cells comprise the Purkinje fibers of the heart.

25. The method of claim 12 wherein said specialized cardiac cells comprise the myocardium muscle layer of the heart.

26. The method of claim 12 further comprising the step of implanting a stent at the site of said occlusion.

27. The method of claim 12 further comprising the step of delivering a drug to the site of said occlusion.

28. The method of claim 12 wherein said occluded artery comprises the sinoatrial nodal artery.

29. The method of claim 12 wherein said occluded artery comprises the conus branch artery.

30. The method of claim 12 wherein said occluded artery comprises the right ventricular artery.

31. The method of claim 12 wherein said occluded artery comprises the right acute marginal artery.

32. The method of claim 12 wherein said occluded artery comprises the atrioventricular nodal artery.

33. The method of claim 12 wherein said occluded artery comprises the right posterior descending artery.

34. The method of claim 12 wherein said occluded artery comprises the first inferior ventricular/lateral artery.

35. The method of claim 12 wherein said occluded artery comprises the second inferior ventricular/lateral artery.

36. The method of claim 12 wherein said occluded artery comprises the third inferior ventricular/lateral artery.

37. The method of claim 12 wherein said occluded artery comprises the atrial circumflex artery.

38. The method of claim 12 wherein said occluded artery comprises the first marginal artery.

39. The method of claim 12 wherein said occluded artery comprises the second marginal artery.

40. The method of claim 12 wherein said occluded artery comprises the third marginal artery.

41. The method of claim 12 wherein said occluded artery comprises the left posterior descending artery.

42. The method of claim 12 wherein said occluded artery comprises the first septal perforating artery.

43. The method of claim 12 wherein said occluded artery comprises the second septal perforating artery.

44. The method of claim 12 wherein said occluded artery comprises the ramus marginals artery.

45. The method of claim 12 wherein said occluded artery comprises the first diagonal artery.

46. The method of claim 12 wherein said occluded artery comprises the second diagonal artery.

47. The method of claim 12 wherein said occluded artery comprises the third diagonal artery.

48. The method of claim 12 wherein said occluded artery comprises the right coronary.

49. The method of claim 12 wherein said occluded artery comprises the left main.

50. The method of claim 12 wherein said occluded artery comprises the left anterior circumflex.

51. The method of claim 12 wherein said occlusion is treated by cutting away at least part of the occlusion.

52. The method defined in claim 12 further comprising the step of delivering a drug to the occlusion.

53. The method of claim 12 wherein said catheter comprises an atherectomy catheter.

54. The method of claim 12 further comprising the step of implanting a stent at the site of said occlusion.

55. The method of claim 12 further comprising the step of delivering a drug to the site of said occlusion.

* * * * *

UNITED STATES PATENT AND TRADEMARK OFFICE
CERTIFICATE OF CORRECTION

PATENT NO. : 5,536,247

DATED : July 16, 1996

INVENTOR(S) : THORNTON

It is certified that error appears in the above-identified patent and that said Letters Patent is hereby corrected as shown below:

At column 4, line 62, "Americas" should be --America,--

Signed and Sealed this

Second Day of March, 1999

Q. TODD DICKINSON

*Attest:*

*Attesting Officer*                *Acting Commissioner of Patents and Trademarks*